United States Patent [19]

Koeniger

[11] Patent Number: 4,565,198

[45] Date of Patent: Jan. 21, 1986

[54] METHOD FOR ALTERING THE CURVATURE OF THE CORNEA

[75] Inventor: Erich A. Koeniger, Metairie, La.

[73] Assignee: Barnes-Hind, Inc., Sunnyvale, Calif.

[21] Appl. No.: 566,105

[22] Filed: Dec. 27, 1983

[51] Int. Cl.$^4$ .................. A61F 17/32; A61B 17/32
[52] U.S. Cl. .................... 128/305; 128/1 R; 623/5
[58] Field of Search ............... 128/1 R, 303 R, 305; 3/13, 1; 604/895, 893, 294; 351/160

[56] References Cited

U.S. PATENT DOCUMENTS

| | | | |
|---|---|---|---|
| 3,488,111 | 1/1970 | Isen | 351/160 |
| 3,831,604 | 8/1974 | Neefe | 604/893 |
| 4,126,904 | 11/1978 | Shepard | 3/13 |
| 4,298,004 | 11/1981 | Schachar et al. | 128/305 |
| 4,327,450 | 5/1982 | Girard | 3/13 |
| 4,343,787 | 8/1982 | Katz | 424/78 |
| 4,346,482 | 8/1982 | Tennant et al. | 3/13 |
| 4,406,285 | 9/1983 | Villasenor et al. | 128/305 |

OTHER PUBLICATIONS

"Thermokeratoplasty in the Treatment of Keratoconus" by A. R. Gasset et al., American Journal of Ophthalmology, vol. 79, No. 2, Feb. 1975, pp. 226–232.

"Corneal Surgery" (Book) by Louis J. Girard, vol. two, published by the C. V. Mosby Co., St. Louis, Toronto, London, 1981, pp. 149–153.

Primary Examiner—Ronald L. Frinks

[57] ABSTRACT

A method for altering the radius of curvature of the cornea which includes the steps of making incisions into the cornea and affixing a rigid gas permeable contact lens, having predetermined radius of curvature, to the eye to have the cornea conform to the shape of the lens.

2 Claims, 4 Drawing Figures

METHOD FOR ALTERING THE CURVATURE OF THE CORNEA

BACKGROUND OF THE INVENTION

1. Field of the Invention

This invention relates to correcting vision defects, such as myopia, and more particularly to changing the radius of curvature of the cornea.

In the normal eye visual perception involves the process of light entering the eye, passing through the cornea and lens converging on the retina at the back of the eyeball. Electrical impulses then transmit a sharp image to the brain.

The common vision problem myopia, or nearsightedness, is a congenital refractive error manifesting itself in the eye's inability to focus light images directly on the retina. Due to the eyeball either being too long or the cornea too curved, the light rays entering the eye converge in front of the retina resulting in the transmission of the brain an "out of focus" image ranging in severity from a mild inconvenience to a debilitating handicap. Ordinarily, myopia can be corrected by corrective lenses, such as eye glasses or contact lenses. However, for many people corrective eyewear is a handicap. Also, when the myopia problem of the eye is the result of a progressive disease such as keratoconus, corrective eye glasses are satisfactory only in the early phases of the disease. Later, when the protrusion of the cornea advances further, contact lens fitting becomes more and more difficult, ultimately necessitating surgery as the only treatment of choice for sight restoration.

2. Description of the Prior Art

Various approaches and devices have been utilized by the prior art for correcting corneal curvature and associated conditions such as myopia, astigmatism and keratoconus. Such approaches included implantation of artificial lenses, implantation of donor's cornea, surgical incisions into the anterior cornea, radio frequency probes, lasers and the like.

One very promising surgical procedure for correcting corneal curvature is radial keratotomy which consists of a series of microsurgical incisions, placed in a radial pattern on the surface of the cornea. The rational for the procedure is as follows. The cornea, being of a dome shape, is being supported by both the limbus and the intraocular pressure. As a result of the microsurgical incisions, the integrity of the cornea decreases resulting in stretching and flattening under the influence of the intraocular pressure. Although initially there appears to be peripheral bulging with central flattening, upon completion of healing the cornea becomes smooth, uniform and as strong as it was prior to the operation. In reducing the curvature of the cornea the result is an improved focusing of the light rays on the retina hence reduction or elimination of myopia. There are, however, clinical variables which influence the success of the surgical procedure, such as intraocular pressure, the radius of corneal curvature and the number of depth of microsurgical incisions made on the cornea. The precise measurement of the variables that affect the outcome is difficult at best. Often, it becomes necessary to repeat the operation in order to further reduce the curvature of the cornea and improve "focusing". One of the most sophisticated techniques in controlling the clinical variables includes the utilization of a special micrometric knife which makes it possible to regulate the incision depth with high precision. The necessary depth of the incision is set according to the degree of myopia, corneal thickness and rigidity, and corneal curvature radius. The expected effect of surgery, given the diameter of the central optical zone, number of incisions and their depth, can then be predicted preoperatively by a computer. While this surgical procedure utilizing the latest instrumental techniques has proved more successful than previous techniques, the lack of predictability of the shape and curvature of the cornea still persists. Obtaining the proper diopter correction is still "an art" and after the healing of the cornea the patient may still be required to wear eye or contact lenses. This lack of reliable predictability greatly hinders the use of this surgical procedure except in serious cases where no other intervention is available.

It is therefore an object of the present invention to provide a reliable method for vision correction.

Figure 1:
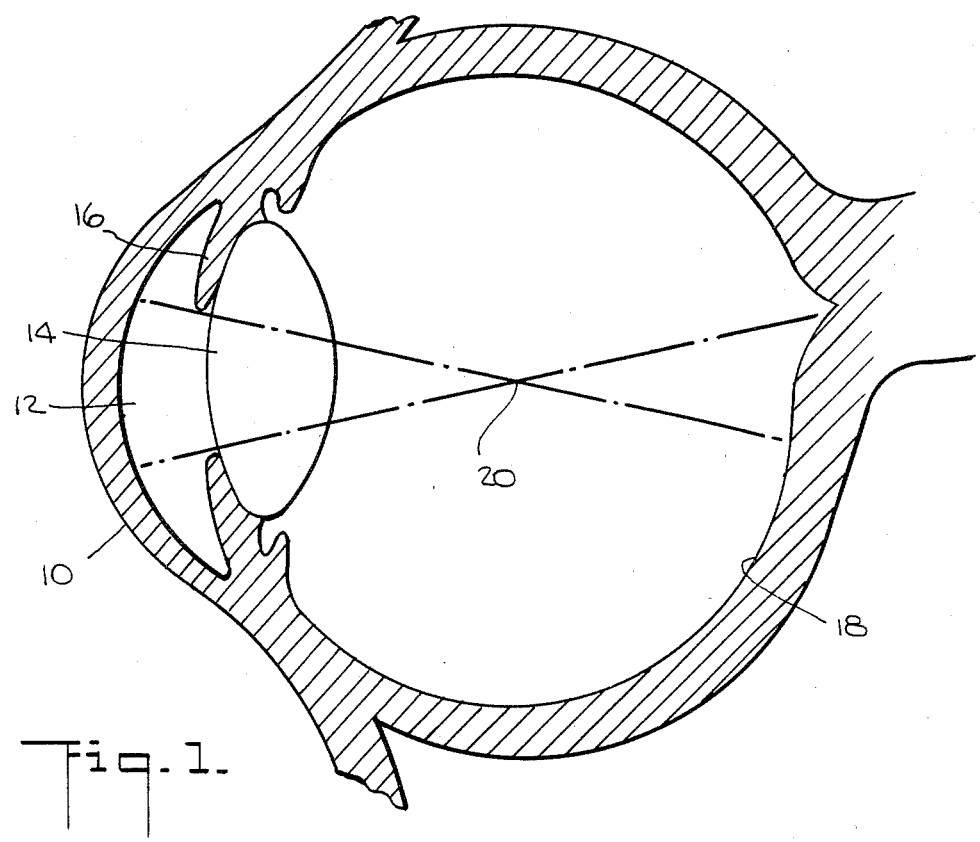
FIG. 1 is a horizontal schematic cross-section through an eyeball.

DETAILED DESCRIPTION OF THE DRAWINGS in FIG. 1, there is illustrated a schematic horizontal cross-section of a human eye having myopia where the numerals represent the following parts of the eye: cornea - 10, pupil - 12, lens - 14, iris - 16, retina - 18, and focal point - 20 at which light rays focus inside the eye. The focal point is substantially distant from the retina resulting in blurred vision. The closer the focal point is to the retina, the clearer the vision becomes.

Figure 2:
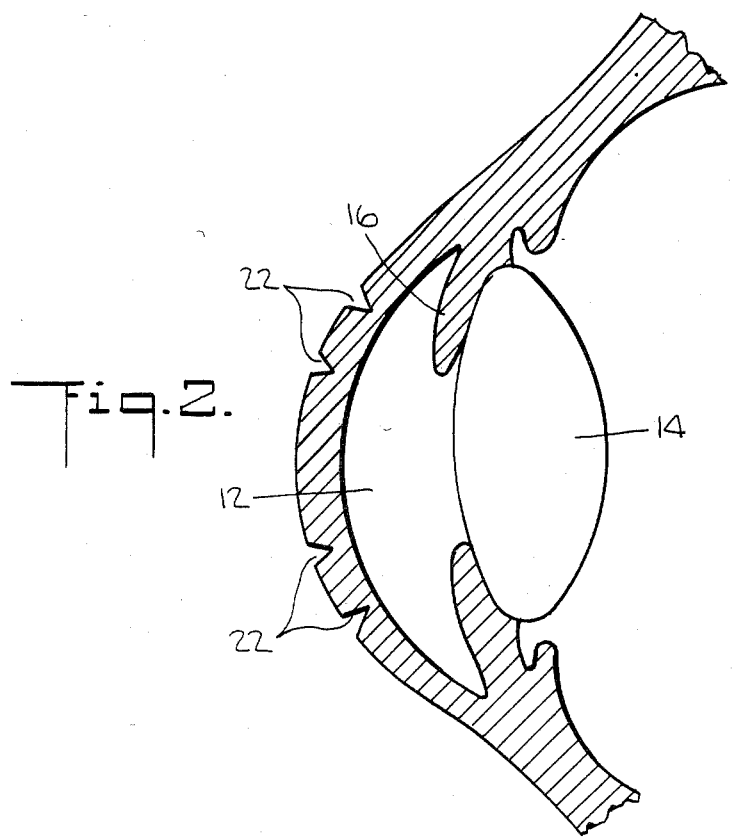
FIG. 2 is a horizontal schematic cross-section through the eyeball showing a portion thereof.

In FIG. 2, there is illustrated a schematic horizontal cross-section of a human eye showing a part thereof, wherein like numerals represent parts of the eye described in FIG. 1, while the numeral 22 represents incisions in the cornea 10.

Figure 3:
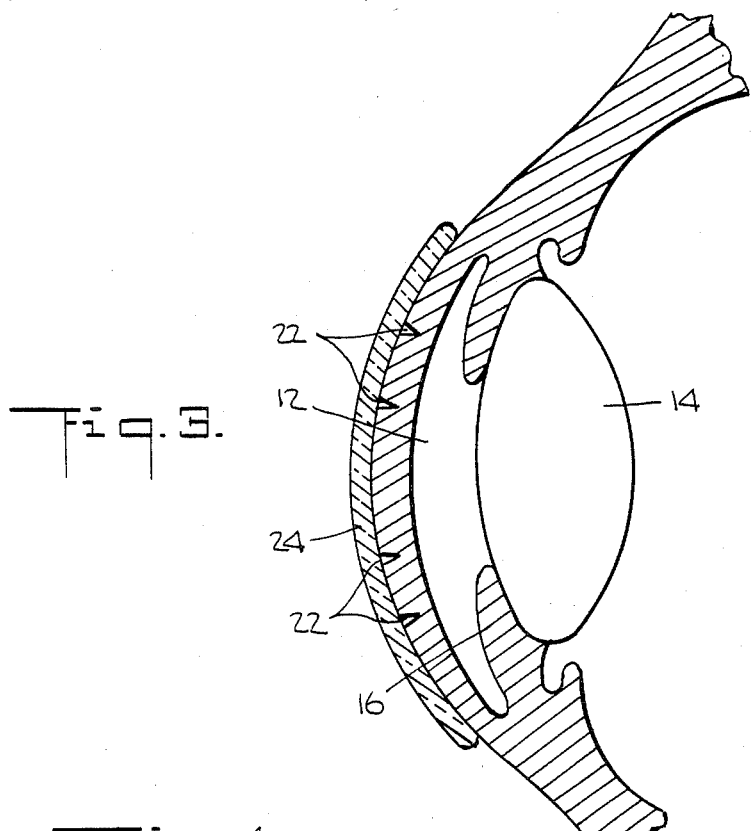
FIG. 3 is a cross-section of the contact lens and cornea showing conformity of the latter to the former.

In FIG. 3, there is illustrated the cornea 10 having incisions 22 and contact lens 24 pressed against cornea 10 so that the same conforms to the configuration of the lens. The contact lens 24 being pressed against the cornea 10 results in the flattening of the cornea.

Figure 4:
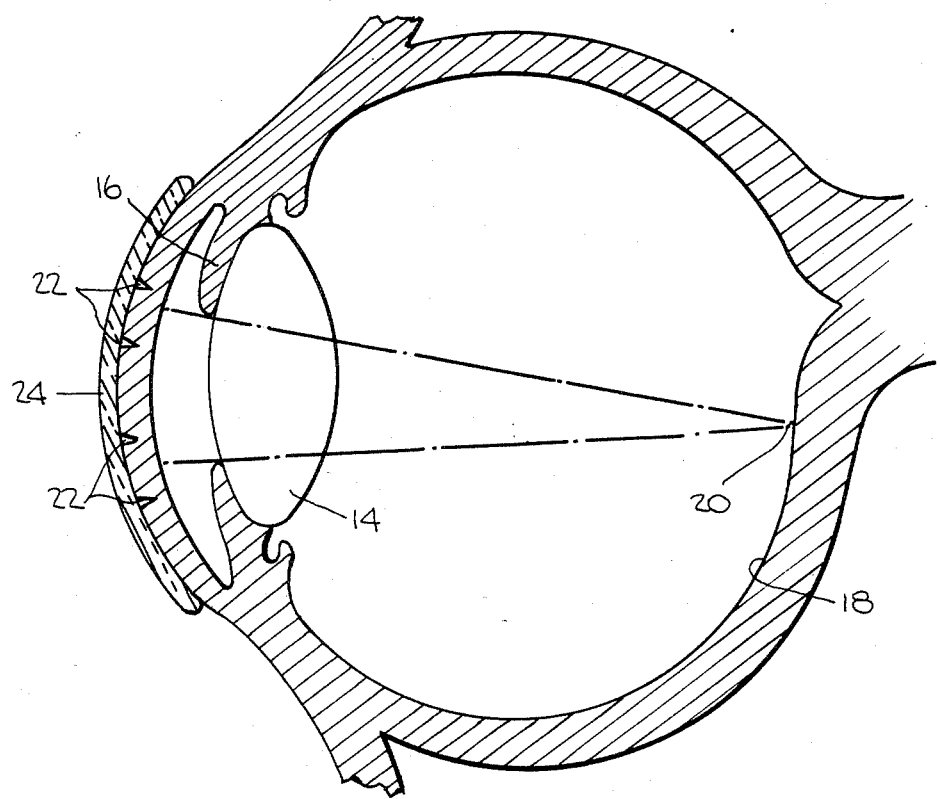
FIG. 4 is a horizontal schematic cross-section through an eyeball having had the corrective surgery of the present invention, showing the incisions in the cornea and the contact lens pressed against the cornea.

FIG. 4 illustrates the desirable consequence of the flattened cornea: the focal point of light rays falls onto the retina.

DESCRIPTION OF THE INVENTION

Briefly stated, the invention concerns a method of correcting the curvature of the cornea comprising the steps of:

a. making incisions into the cornea using microsurgical technique;

b. affixing a rigid gas permeable contact lens, having a predetermined radius of curvature, to the eye following surgery;

c. applying light pressure on the contact lens so that the cornea will conform to the shape of the lens;

d. allowing the cornea to heal under the applied pressure; and e. after healing, removing the contact lens from the eye.

In accordance with the present invention, measurements with a Keratometer of the corneal curvature is made and the correction factor necessary to obtain proper focusing is calculated. Based on the calculated result, the corrective corneal lens having the necessary diopter is selected for use following the operation.

The lens used in the method of the present invention should have a diameter of between 10.5 to 12.00 mm and should have an aspheric type base curve with an optical zone of about 6.0 mm. The optical zone of the lens should have sufficient rigidity to resist flexing or warping.

The lens used in the method of the present invention may be fabricated from rigid plastic materials such as hydrophobic acrylic-type polymers as polymethyl methacrylate and the like. Lenses of this type have been known for many years and their fabrication technique is well known in the prior art.

The lens used in the method of the present invention may also be fabricated from semi-rigid polymeric materials such as cellulose acetobutyrate, and silicone rubber.

Soft contact lens materials consisting of hydrogels of hydrophobic polymers may also be used for fabricating corrective cornea lenses when the diopter required to obtain corrected vision is small.

The lenses are conventionally made by marching blanks or disks obtained by polymerizing a synthetic monomeric composition. The machining operation imparts the final shape with the required optical properties to the lenses.

The preferred method of accomplishing the objective of the present invention includes cutting out a wedge of the cornea in the flattest meridian on both sides of the pupil followed by placing the corrective contact lens on the cornea and applying sufficient pressure thereon so that the wedges will close. The contact lens may be affixed to the cornea surgically (such as suturing) or by bandaging the eye using conventional eye bandaging techniques. The number of incisions may be increased when necessary to accomodate the cornea upon stretching due to the pressure exerted thereon by the contact lens. The number and kind of incisions is determined by the operating surgeon from the readings of the keratometer, the internal pressure of the eye and other data obtained from the examination of the patient's eye.

The lens is maintained affixed to the patient's eye until the epithelium heals, usually within four to six days.

What is claimed is:

1. A method for altering the radius of curvature of a cornea comprising the steps of
    a, measuring the corneal curvature with a keratometer;
    b, calculating the correction factor necessary to obtain proper focusing;
    c, making sufficient incisions into the cornea to allow reduction of its curvature as determined by the correction factor calculated in step b;
    d, placing a rigid gas permeable contact lens, having a radius of curvature, on the eye, said radius having been determined by using the correction factor calculated in step b;
    e, applying light pressure on the contact lens by bandaging technique or surgical suturing so that the cornea will conform to the shape of the lens;
    f, allowing the cornea to heal under the applied pressure; and
    g, after healing, removing the contact lens from the eye.

2. A method of decreasing the radius of curvature of a cornea comprising the steps of:
    a, measuring the corneal curvature with a keratometer;
    b, calculating the correction factor necessary to obtain proper focusing;
    c, removing, by cutting, at least one wedge of the cornea in the flattest meridian on both sides of the pupil to allow reduction of the curvature of the cornea as determined by the correction factor calculated in step b;
    d, placing a corrective rigid, gas permeable contact lens onto the cornea, said corrective rigid, gas permeable contact lens having a radius that has been determined by using the correction factor calculated in step b;
    e, applying sufficient pressure on the contact lens by bandaging technique or surgical suturing to effect closing of the wedges;
    f, allowing the cornea to heal under the applied pressure; and
    g, after healing, removing the contact lens from the cornea.

* * * * *